United States Patent

Klemarczyk et al.

[11] Patent Number: 4,728,709
[45] Date of Patent: Mar. 1, 1988

[54] TERMINAL CLUSTER VINYL SILICONES AND ACRYLATE CLUSTER SILICONES THEREFROM

[75] Inventors: Philip Klemarczyk, Newington, Conn.; Samuel Q. S. Lin, Edgewater, N.J.

[73] Assignee: Loctite Corporation, Newington, Conn.

[21] Appl. No.: 807,933

[22] Filed: Mar. 10, 1986

Related U.S. Application Data

[60] Division of Ser. No. 623,759, Jun. 22, 1984, Pat. No. 4,575,546, which is a continuation-in-part of Ser. No. 515,702, Jul. 20, 1983, Pat. No. 4,504,629, and a continuation-in-part of Ser. No. 571,036, Jan. 16, 1984, Pat. No. 4,675,346, and a continuation-in-part of Ser. No. 575,256, Jan. 30, 1984, Pat. No. 4,503,208.

[51] Int. Cl.$^4$ .................. C08F 230/08; C08F 275/00; C08G 77/20
[52] U.S. Cl. ...................... 528/15; 525/193; 525/289; 525/288; 525/477; 525/479; 526/245; 526/279; 528/26; 528/32; 528/901
[58] Field of Search .............. 526/279, 245; 528/901, 528/32, 15, 26; 525/477, 193, 284, 288, 479

[56] References Cited

U.S. PATENT DOCUMENTS

| | | | |
|---|---|---|---|
| 4,364,809 | 12/1982 | Sato et al. | 526/279 |
| 4,529,629 | 7/1985 | Liu | 528/15 |
| 4,591,608 | 5/1986 | Okinoshima | 522/13 |
| 4,595,635 | 6/1986 | Dubrow et al. | 522/65 |

*Primary Examiner*—Hebert J. Lilling
*Attorney, Agent, or Firm*—Vidas & Arrett

[57] ABSTRACT

A polyorganosiloxane polymer having a structure represented by one of the formulas

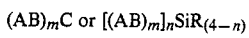

$(AB)_mC$ or $[(AB)_m]_n SiR_{(4-n)}$ where the R groups are the same or different organic groups other than acrylic groups or groups co-curable therewith; A is a linear polyorganosiloxane segment containing between 3 and about 50 siloxane repeat units at least 3 of which are acrylic group containing repeat units represented by the formula

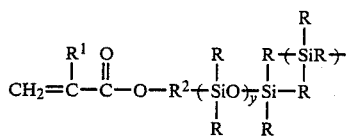

where $R^1$ is lower alkyl, the $R^2$ groups are the same or different alkylene, alkyleneoxy or alkenylene groups, and y is 0–4; B is a polyorganosiloxane segment represented by the formula

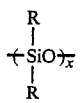

where x is an integer of at least 100; C is A or a triorganosilyl group; m is an integer of 1 or more; and n is 3 or 4.

5 Claims, No Drawings

TERMINAL CLUSTER VINYL SILICONES AND ACRYLATE CLUSTER SILICONES THEREFROM

This application is a division of Ser. No. 623,759, filed June 22, 1984, now U.S. Pat. No. 4,575,546, which is a continuation-in-part of application Ser. No. 515,702 filed July 20, 1983, now U.S. Pat. No. 4,504,629; Ser. No. 571,036, filed Jan. 16, 1984 now U.S. Pat. No. 4,675,346 and Ser. No. 575,256, filed Jan. 30, 1984, now U.S. Pat. No. 4,503,208.

FIELD OF THE INVENTION

This invention pertains to acrylic functional silicones, compositions thereof and cure products therefrom.

CROSS-REFERENCE TO RELATED APPLICATIONS

The present invention is related to the inventions described in the concurrently filed applications of S. Lin titled Curable Cluster Silicones, Ser. No. 623,791 abandoned, June 22, 1984, and of S. Kakos and S. Lin titled Terminal Cluster Acrylate Silicones, Ser. No. 623,760, now U.S. Pat. No. 4,575,545 both of which are based on the same disclosure hereof.

BACKGROUND OF THE INVENTION

Acrylic functional organosiloxane polymers (silicones) are well known. Such materials have found particular use as components of radiation-curable release coatings for which bulk cured properties have little importance.

In U.S. Pat. No. 3,886,865 there are described compositions useful for producing ink repellent areas on a printing plate which are solutions of certain methacrylate functional silicones. The silicones are essentially solid materials which may be produced by condensation of a hydroxy or chloro terminated dimethylsilicone with a hydrolyzate of phenyltrichlorosilane and methacryl functional silanes having three hydrolyzable groups. The trifunctional ingredients will produce highly cross-linked polymers of undefined structure which are nonflowable at room temperature.

In U.S. Pat. No. 4,387,240 there are described low molecular weight oligomers having a high methacrylate density which may be represented by the formula:

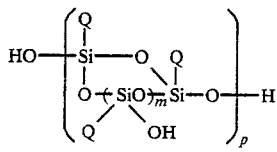

where m is 1, 2 or 3; p is 2–10 and Q is methacryloxy propyl or similar groups. These oligomers are used as binders in dental filling compositions to give hard abrasion resistant cured fillings.

In U.S. Pat. No. 4,424,328 there are described branched low molecular weight siloxane compounds with 3 or 4 of the branches terminated with methacryloxypropyl groups. These compounds are used in the preparation of hard contact lenses.

In U.S. Pat. No. 4,035,355 there are described anaerobically cured acrylic functional silicone resins. These are randomly copolymerized materials which must have a minimum functionality, as defined in that reference, of 2.2 to cure. These resins have very high cross-link density which will result in rigid cured products.

In co-pending application Ser. No. 571,036, filed Jan. 16, 1984, there are described reinforced compositions of UV curable silicones having terminal acrylic groups and elongated acrylate-free intermediate regions which cure under UV irradiation to tough rubbers. The low acrylic functionality density of these resins, however, makes it difficult, if at all possible, to cure them with chemical free radical generators at ambient temperatures.

There therefore exists a need for silicone resins which can be cured to tough rubbery products by chemical free radical generators, particularly anaerobic cure systems. There also exists a need for UV curable acrylic silicone polymers of higher molecular weight or which may be cured to rubbery products at faster speed.

It is an object of this invention to produce an acrylic functional silicone polymer, curable to an elastomer, which has a liquid flowable consistency and which can be readily cured even by chemical free radical generators at ambient temperatures. The inventive polymers extend the range of molecular weight of acrylated silicone polymers which may be cured to tough rubbers by UV irradiation. These objects and others which will become apparent from the following discussion are met with novel "cluster" acrylic silicone resins of the present invention.

SUMMARY OF THE INVENTION

The silicone resins of the present invention are silicones in which a plurality of acrylic groups are clustered at or near the chain ends of the silicone polymer. More specifically, the silicones are polyorganosiloxanes characterized by a 25° C. flowable viscosity below about 500,000 cps which may be represented by one of the formulas:

$$(AB)_m C \quad \text{[I]}$$

or $$[(AB)_m]_n SiR_{(4-n)} \quad \text{[II]}$$

where A is a linear, branched or cyclic organosiloxane segment of no more than about 50 siloxane repeat units which contains 3 or more acrylic groups thereon; B is an organosiloxane polymer segment represented by the formula $-(SiR_2O-)_x$; the R groups are the same or different organo groups other than acrylic groups or groups co-curable therewith, preferably substituted or unsubstituted alkyl or aryl groups; x is an integer of at least 100; C is A or a triorganosilyl group; m is an integer of 1 or more, typically 1–4; and n is 3 or 4.

DETAILED DESCRIPTION OF THE INVENTION

The concept forming the basis of this invention is that a combination of fast curing and elastomeric cured properties can be obtained in the liquid silicone if the silicone is structured so as to have long unreactive siloxane segments which are terminated by clusters of closely spaced reactive acrylic sites. The cluster regions are more readily cross-linked by UV irradiation or chemical free radical generators than corresponding monoacrylate terminated silicones, while the long unreactive silicone segments provide elastomeric cured properties.

By acrylic containing group is meant a group which includes a radical represented by the formula $CH_2=C(R^1)-C(=O)-$, where $R^1$ is H, or lower alkyl. This acrylic structure is hereinafter also represented by the abbreviation Acr. Typically the acrylic containing group will be bound to a silicon atom of the siloxane polymer through a C—Si linkage. Such groups may be represented as $$Acr-X-R^2- \qquad [III]$$

where X is O, NH or S and $R^2$ is alkylene or alkenylene such as propylene or propenylene. Less preferably, the acrylic group may be linked to silicone through a C—O—Si linkage. Such groups may be represented by the formulas:

$$Acr-O- \qquad [IV]$$

and $$Acr-O-R^2-O- \qquad [V].$$

These groups, although hydrolytically unstable, may be usefully employed in limited amounts in the inventive polymers.

As still another alternative the acrylic containing group may be represented by the structure:

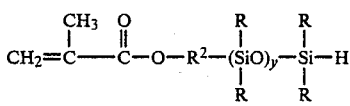  [VI]

where y is 0 to 4. As taught in U.S. Pat. No. 4,504,629, the disclosure of which is incorporated herein by reference, such groups may be produced by hydrosilation of a vinyl or other alkenyl or alkynyl functional silicone with a grafting agent represented by the formula:

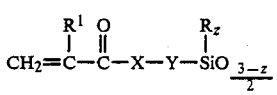  [VII]

In general the A segments may be defined as including at least 3 acrylic containing siloxane units of the structure

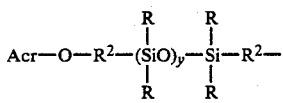  [VIII]

where R, $R^1$ and X are as previously defined, Y is a divalent linking group and z is 0, 1 or 2.

The A segment may be cyclic linear or branched. When cyclic, the A segment will include at least 3 siloxane units as in the formula VIII and at least one linking unit as discussed below. When linear or branched, the A segment will preferably include, in addition to a linking unit and at least 3 units of formula VIII, a plurality of units of the formula

  [IX]

where a is 0–3. Preferably the units of formula (IX) will comprise about 40–70% of the linear or branched A segment repeat units and the units of formula (VIII) will comprise about 30–60% of the A segment repeat units, and the respective units will be alternately or randomly distributed. It is also preferred that the total number of repeat units on the A segment be less than 30, still more preferably about 20 or less in order to provide a more concentrated cross-linking regions.

As mentioned, the A segments will include linking units which bind to the B segments. The linkage may be through either Si—O—Si bonds or Si—$R^3$—Si bonds where $R^3$ is alkylene or alkenylene. Examples of such linkages include formulas X–XII below where the open valencies connect to other A segment repeat units and B is as defined for formulas I and II.

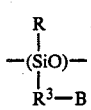  [X]

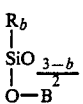  [XI]

where b is 1 is or 2.

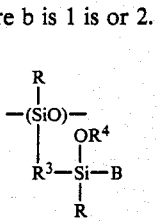  [XII]

where $R^4$ is alkyl, substituted alkyl, or Acr—O—$R^2$—.

The B Segments in formulas I and II, above, are most conveniently comprised of dimethylsiloxy units. However, it may be desirable in some instances to substitute other groups for one or both of the said methyl groups in the B segment. For instance, silicones containing phenyl groups are well known for increased compatibility with organic compounds or with other silicones having significant amounts of organic functional groups. Thus, it may be desirable in some instances for the B segment to be comprised of some or all diphenyl siloxy or methyl phenyl siloxy repeat units so as to decrease phase separation of the A and B blocks in the cured polymer or to increase the solubility of curing or stabilizing agents in a composition of the inventive cluster silicones.

Other R groups which may be substituted for methyl on the B segment siloxy units are other alkyl groups or substituted alkyl or aryl groups such as trifluoropropyl. The B segment groups, however, should not be co-reactive under free radical cure conditions with the acrylic groups of the A segment since the B segment must remain uncrosslinked when the resin is cured in order to obtain the desired elastomeric properties. Examples of groups co-curable with acrylic groups are other ethylenically unsaturated groups such as vinyl or allyl and crosslinking groups such as alkyl thiol.

While the B segments may have a minimum of about 100 repeat units and still cure to useful elastomeric products, at least when the A segments are about 25 linear units or less, it is preferred that they have at least about 160 repeat units, still more preferably at least about 300 repeat units, in order to give optimal cure elastomers.

The inventive cluster acrylated silicones may be synthesized by a number of routes including coupling of a multi-acrylate cluster to an acrylate free silicone terminated with a suitable functional group which can add to or condense with a corresponding reactive group on the multi-acrylate cluster. Where the multi-acrylate cluster has exactly one such coupling functional group it can be added essentially quantitatively to a difunctional acrylate free silicone to produce a resin as in formula I where C is an A segment. However, it is generally more practical to synthesize a multi-acrylate cluster with such coupling functionalities present at an average of greater than one, typically about 1.5, group per cluster in order to assure at least 1 such coupling group on each cluster. When clusters with plural coupling functionality are used, viscosity increasing chain extension can occur. Such a chain extension can be controlled, however, by converting a portion of the reactive ends of the acrylate free silicone polymer to nonreactive ends (i.e., nonreactive to the coupling reaction). Thus a silanol terminated dimethylsilicone may be reacted with up to 1 mole of trimethylmethoxysilane or methacryloxypropyldimethylchlorosilane before coupling to a multi-acrylate cluster with one or more condensable groups. In such case the coupled resin is represented by formula I where C is triorganosilyl.

In accordance with the invention, a variety of novel silicones have been separately developed of which the following species are exemplary.

(a) Methacrylate Cluster Silicones From Silicones With Terminal Vinyl Clusters

In co-pending application Ser. No. 515,702 of July 20, 1983, there are described hydrosilation reagents such as those of formula VII above containing methacrylate functionality which can be added to vinyl silicones so as to create novel acrylic functional silicones. Examples of these reagents are 3-(methacryloxypropyleneoxy)-1,1,3,3-tetramethyldisiloxane, methacryloxypropyl-dimethylsilane and 3-(methacryloxypropenyl)-1,1,3,3-tetramethyldisiloxane. These same reagents can be utilized to convert silicones having terminal vinyl clusters to terminal cluster acrylated silicones of this invention.

Cluster vinyl silicones may be prepared by several methods. The simplest such clusters are trivinylsiloxy terminated dimethyl silicones such as described in U.S. Pat. No. 4,364,809. Because of the bulkiness of the hydrosilation reagents utilized to create the inventive acrylate clusters from vinyl cluster silicones however, it is more preferable that the cluster vinyl silicones have the multivinyl functionality spread among several siloxy units, rather than on a single molecule. Such silicones can be prepared by sequential anionic polymerization of a mixture of cyclic dimethylsiloxanes and vinyl containing cyclic siloxanes followed by extension of additional cyclic dimethylsiloxanes to form the B segments, as exemplified in Example 1 below. An alternative synthesis of cluster vinyl terminated silicones is to prepare a alkenyl or alkynyl containing segment by base catalyzed equilibrium polymerization of alkenyl or alkynyl silanes or low molecular weight organosiloxanes followed by coupling with a silicone terminated with condensable groups. Example 2 illustrates the preparation of a cluster vinyl silicone by this alternative method. Example 3 illustrates the preparation of a cluster acrylated silicone of the present invention from a vinyl cluster silicone.

The cluster vinyl products produced by the exemplified methods may be represented by the formula

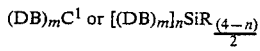

where B, R, m and n are as previously defined, $C^1$ is D or a triorganosilyl group; and D is a linear organosiloxane segment containing between about 3 and about 50 repeat units at least 3 of which contain pendant vinyl, allyl or other alkenyl or alkynyl groups.

EXAMPLE 1

A dry 100 ml three neck flask, equipped with a mechanical stirrer, condenser, thermometer, addition funnel and nitrogen blanket was charged with hexamethylcyclotrisiloxane (22.2 g, 0.1 mole), 1,3,5-trimethyl-1,3,5-trivinylcyclotrisiloxane (5.2 g, 0.02 mole) and dry THF (250 ml). A 1.2M solution of n-butyllithium (4.8 ml, 6 mmole) was added at room temperature, and after stirring for five minutes, the reaction temperature was raised to 45°–50° C. The reaction mixture was stirred at 45°–50° C. for 90 minutes and additional hexamethylcyclotrisiloxane (111.0 g, 0.5 mole) in 250 ml of THF was added dropwise. Stirring and heating was continued for 90 minutes. Silicon tetrachloride (0.29 g, 1.7 mmole) was added and the temperature was raised to reflux (ca. 65° C.) for 18 hours. THF was removed under reduced pressure and the residue taken up in 500 ml of toluene. The toluene mixture was washed once with 250 ml of 5% aqueous sodium bicarbonate solution and then washed with water to neutrality. The organic layer was separated, dried (MgSO$_4$) and filtered. Solvent was removed under reduced pressure, and the product vacuum dried for 3 hours at 75° C. and 0.2 mm/Hg. Yield=110 g (80%). Theoretical MW=100,000: found GPC MW(wt. average)=63,000 (polystyrene standard).

EXAMPLE 2

A dry three liter resin kettle, equipped with a mechanical stirrer, condenser, thermocouple temperature controller and nitrogen blanket, was charged with octamethylcyclotetrasiloxane (37.0 g, 125 mmole), 1,3,5,7-tetramethyl-1,3,5,7-tetravinyl-cyclotetrasiloxane (22.2 g, 62.5 mmole), and α,ω-bis-(N,N-dimethylamino)-octamethyltetrasiloxane (25 g, 62.5 mmole). This reaction mixture was heated to 80°–89° C. with stirring and tetramethylaminosilanolate (2.0 g) was added. Viscosity increased with time. After stirring overnight at 80°–85° C., the reaction mass was heated to 150°–155° C. for three hours to destroy the catalyst. Volatile components were removed by heating the crude product to 90° C. for two hours at 0.5 mm/Hg. Yield=73.4 g (89%). Found GPC MW(no. ave.)=2900.

A dry 250 ml three neck flask, equipped with a mechanical stirrer, condenser, thermometer and nitrogen blanket, was charged with Rhone-Poulenc 48V3500, a 28,000 mw polydimethylsiloxane terminated with silanol groups, (80 g), the polymer of the previous paragraph (6.5 g), and toluene (100 ml). The solution was heated to reflux for 18 hours. The reaction was quenched with 1 ml of n-butanol and stirred for 30 minutes at reflux. Solvent was removed under reduced pressure and the product vacuum dried for three hours at 50° C. and 0.2 mm/Hg to give 61.3 g of a cluster vinyl terminated liquid silicone polymer. No. Ave. MW found (GPC polystyrene std.)=79,000.

EXAMPLE 3

A dry 250 ml three neck flask, equipped with a magnetic stirrer, condenser, thermometer and nitrogen blanket was charged with the polymer of Example 1 (30 g, 0.3 mmol), methacryloxypropyleneoxydimethylsilane (2.6 g, 13 mmol), toluene (100 ml), and BHT (0.04 g) as stabilizer. A sample of this solution was taken for IR analysis. Catalyst (2% $H_2PtCl_6.6H_2O/CH_3COOC_4H_7$) was added and the reaction mixture was heated to 70°-75° C. The reaction was complete after 90 minutes as shown by the disappearance of the Si-H absorption in the IR spectrum of the solution. The solution was filtered and solvent removed under reduced pressure. The product was vacuum dried for three hours at 50° C. and 0.8 mm/Hg. Yield=31.3 g (96%). Theoretical MW=64,000: found GPC MW(wt. average)=81,967.

(b) Acrylate Cluster Silicones From Vinyl Terminated Silicones

The hydrosilation addition reaction can also be used to prepare acrylate clusters from readily available monoalkenyl terminated silicones. Such silicones are typically terminated with vinyldimethylsilyl or vinyldiphenylsilyl groups. Silicones terminated with other groups such as allyl groups may also be used. This procedure uses a short siloxane segment with multiple SiH functionality, some of which are used to bind acrylic groups to the short segment and some of which are used to bind the short segment to the vinyl terminated silicone polymer. Thus, vinyl terminated silicones may be hydrosilated using a large excess of a short chain silicone having three or more SiH functional groups per molecule. Cyclic silicones such as $D_4^{4H}$ and $D_5^{5H}$ are especially useful as short segment silicones for this method. The SiH functional silicone is used in substantial excess so as to allow only minimal chain extension, resulting in silicones containing terminal regions having plural SiH functionality. This functionality is then used to hydrosilate an alkenyl or alkynyl acrylate monomer, such as allyl methacrylate, allyloxyethyl methacrylate, propargyl acrylate or propargyl methacrylate to produce the inventive cluster acrylate silicones. Example 4 illustrates a synthesis in accordance with this method.

EXAMPLE 4

Mobay U-1, a vinyl-terminated silicone of approximately 26,000 MW (25.0 g, $1.89 \times 10^{-3}$ eq vinyl) was added to 0.68 g ($1.135 \times 10^{-2}$ eq.SiH) tetramethylcyclotetrasiloxane and 0.34 g 2% chloroplatinic acid hexahydrate in butyl acetate to 25 ml toluene. The mixture was heated to 100° C. for 3 hours with stirring under nitrogen. The reaction was cooled to 70° and 1.25 g (0.011 mole) propargyl acrylate with 0.01 g butylated hydroxytoluene (BHT) were added. Heating was continued at 70° C. for 3 hours when IR showed no SiH left in the reaction. The reaction was then deep-stripped under high vacuum to give 26.8 g of a viscous, translucent liquid. This material, with 2% of the photoinitiator diethoxyacetophenone (DEAP), was cured by 70 mw/cm² UV to a stretchy elastomer, 5 seconds per side onto a 3/16" sample.

Alternatively, the hydrosilation steps may be reversed, first reacting the short chain SiH silicone with the acrylic monomer and then adding the vinyl terminated silicone. This procedure, however, is limited to methacrylate or other alpha-alkyl acrylate monomer hydrosilations since the SiH functionality reserved for addition to the vinyl silicone will attack acrylate under these extended two-step hydrosilation conditions.

(c) Acrylate Cluster Silicones From Silanols and Condensable Acrylic Clusters

This method involves preparation of a short chain plural acrylated silicone segment which has condensable functionality followed by condensation of the resulting acrylate cluster with a longer silanol terminated silicone. Example 5 illustrates one method by which the acrylic and condensable functionalities are separately selected and added to a short chain SiH functional silicone, followed by condensation with a partially end blocked silanol.

EXAMPLE 5

Pentamethylcyclopentasiloxane (25.0 g, 0.083 mole) was placed in a 250 ml 3 neck flask containing 17.57 g (0.124 mole) vinylmethyldichlorosilane, 42.2 g toluene, and 0.1 g of a divinyltetramethyldisiloxane/platinum catalyst in xylene, giving 50 ppm platinum in the reaction. The reaction was heated to 80° C. under nitrogen with stirring, resulting in an exotherm to 86° C., lasting 20 minutes. After 10 more minutes 35.18 g (0.320 mole) propargyl acrylate with 0.05 g BHT was added and the reaction temperature raised to 90° C. for 3 hours. IR showed complete disappearance of SiH at this time. This reaction mixture comprises a 62.1% solution of an acrylated cyclic containing 1.5 methyldichlorosilyl groups per ring.

Rhone Poulenc silanol-terminated silicone 48V3500 (25.0 g, $1.765 \times 10^{-3}$ eq Silanol) was added to a solution of 0.18 g ($0.882 \times 10^{-3}$ mole) acryloxypropenyldimethylchlorosilane and 0.4 g (0.005 mole) pyridine in 25 ml hexane and stirred 30 minutes at 60° under nitrogen. Pyridine hydrochloride gradually separated. The following reagents were added successively, allowing 30 minutes at 60° for reaction between each addition: the reaction product mixture from the previous paragraph, (1.27 g solution, $2.64 \times 10^{-3}$ eq SiCl); 0.23 g ($1.76 \times 10^{-3}$ mole) 2-hydroxypropyl acrylate; 2.0 g (0.027 mole) 1-butanol. After the last addition and reaction increment, the mixture was filtered through Celite TM and stripped under high vacuum to give 24.0 g of a hazy, flowable liquid that readily cured by 70 mw/cm² UV (2% DEAP) to a stretchy elastomer in only 5 seconds irradiation per side onto a 3/16" thick sample.

It is known from co-pending applications Ser. Nos. 509,568, filed June 30, 1983 and 575,256, filed Jan. 30, 1984, the disclosures of which are incorporated herein by reference, and from references cited therein that hydrosilations involving allyl methacrylate suffer from the limitation that substantial amounts of the hydrosilation product result in silyl methacrylate groups due to propene elimination. Typically about 30% of the hydrosilation product undergoes propene elimination. These silyl methacrylate groups are usually undesirable because of their reactivity to moisture, similar to the well known acetoxy silicones. Example 6, however, illustrates that this previously undesired characteristic can be exploited to prepare cluster acrylated silicones utilizing the silyl methacrylate groups obtained from an allyl methacrylate hydrosilation as the leaving groups in a subsequent silanol condensation.

EXAMPLE 6

A mixture of 37.6 g of an SiH containing dimethyl silicone (M.W. 2654, $2.5 \cdot 10^{-3}$ eq/g SiH), 12.2 g allyl methacrylate, 0.25 g BHT, 0.126 g of $H_2PtCl_6/C_8H_{17}OH$ in toluene (0.76% Pt by weight) was placed in a 500 ml flask which was equipped with a condensor with a $N_2$ inlet, a mechanical stirrer, and a thermometer. The temperature was raised to 70° C. gradually, and an exotherm was observed. The mixture was heated at 75° C.±5° C. for two hours and IR of SiH absorption showed the reaction was about 50% complete. Two grams more of allyl methacrylate was added and the reaction continued for another hour. IR showed 60% completion.

Then 200 g of a 28,000 MW silanol terminated silicone in 100 ml toluene was added to couple the prepolymer of the previous reaction. The coupling was continued at 75° C.±5° C. for 3 hours. After stripping toluene at 70° C., it gave a colorless flowable liquid. An aliquot with 1.5% by weight DEAP was prepared and exposed to 70,000 uw/cm² UV for 30 seconds to give a jelly-like material.

(d) Cluster Acrylated Silicones From Condensation of Silanol Silicone and Acrylated Hydrolyzable Silanes This procedure involves condensation of a mixture of multifunctional (D,T or Q) silanes on the ends of a silanol terminated silicone, followed by capping with a monofunctional (M) silane. Acrylated M, D or T silanes are included in the mixture to provide the desired multiple acrylate terminal clusters.

EXAMPLE 7

Rhone-Poulenc 48V3500 (100.0 g, $7.06 \times 10^{-3}$ eq silanol) was mixed with 2.10 g (0.014 mole) methyltrichlorosilane, 14.57 g (0.113 mole) dimethyldichlorosilane, and 3.15 g (0.014 mole) acryloxypropenylmethyldichlorosilane, all in 200 ml hexane. Pyridine (0.8 g, 001 mole) was added to the nitrogen blanketed, mechanically stirred solution, and the reaction continued for one hour at 70° C. Next, 4.55 g (0.022 mole) acryloxypropenyldimethylchlorosilane was added followed by the portionwise addition of 26.72 g (0.318 mole) sodium bicarbonate, allowing for effervescence. After one hour at 60° C. after the last portion of bicarbonate, the reaction was filtered through Celite TM and stripped under high vacuum to give 76.0 g of a clear, flowable liquid that clouded on cooling. It was cured by 70 mw/cm² UV as per the previous examples to a soft elastomer, requiring 20 seconds of radiation per side.

We claim:

1. A polyorganosiloxane polymer having terminal vinyl clusters represented by the formula $$(DB)_m C^1 \text{ or } [(DB)_m]_n SiR_{(4-n)/2}$$

where the R groups are the same or different organic groups other than acrylic groups or groups co-curable therewith; B is a polyorganosiloxane segment represented by the formula $$\left(\begin{array}{c} R \\ | \\ SiO \\ | \\ R \end{array}\right)_{\overline{x}}$$

where x is an integer of at least 100; $C^1$ is D or a triorganosilyl group; m is an integer of 1 or more; n is 3 or 4; and D is a linear polyorganosiloxane segment containing between 3 and about 50 siloxane repeat units at least 3 of which contain pendant alkenyl or alkynyl groups.

2. An organosiloxane block copolymer comprising:
   (a) at least one siloxane block having at least 100 siloxane units, said units having the formula $R_2SiO$,
   (b) at least one siloxane block consisting of between 3 and 50 siloxane units of the formula:

$$R^1_2SiO$$

and, optionally,
   (c) a siloxane block comprising a siloxane unit of the formula $$RSiO_{1.5} \text{ or } SiO_2$$

where R is alkyl, substituted alkyl or aryl; and the $R^1$ groups are the same or different R, alkenyl groups or alkynyl groups, provided that at least 3 units $R^1_2SiO$ include an alkenyl or alkynyl group.

3. A block copolymer as in claim 2 where at least 3 units of the formula $R^1_2SiO$ include a vinyl group.

4. A composition comprising a block copolymer as in claim 2, a siloxane compound with silicon hydride functionality and a hydrosilation catalyst.

5. A composition as in claim 4 where at least 3 units $R^1_2SiO$ of the block copolymer include a vinyl group.

* * * * *

UNITED STATES PATENT AND TRADEMARK OFFICE
CERTIFICATE OF CORRECTION

PATENT NO. : 4,728,709
DATED : March 1, 1988
INVENTOR(S) : Philip Klemarczyk and Samuel Q. S. Lin It is certified that error appears in the above-identified patent and that said Letters Patent is hereby corrected as shown below:

Col. 1, line 22, "Kakos" should be -- Nakos --.

Col. 6, line 21, "1.2M" should be -- 1.25 --.

Abstract of the Disclosure, second formula:

"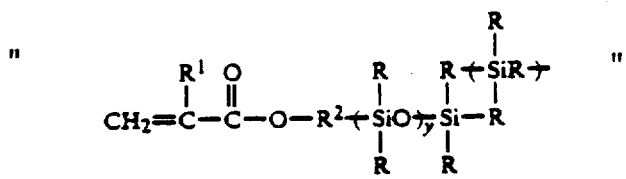"

should be

-- 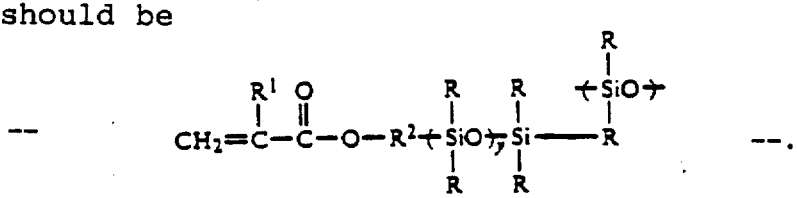 --.

Signed and Sealed this

Sixteenth Day of August, 1988

Attest:

DONALD J. QUIGG

Attesting Officer

Commissioner of Patents and Trademarks